(12) United States Patent
Bashiardes et al.

(10) Patent No.: US 6,407,110 B2
(45) Date of Patent: Jun. 18, 2002

(54) POLYHYDROXYALKYLPYRAZINE DERIVATIVES AND THEIR PREPARATION AND MEDICINES CONTAINING THEM

(75) Inventors: Georges Bashiardes, Poitiers; Jean-Christophe Carry, Saint Maur; Michel Evers, La Queue en Brie; Bruno Filoche, Creteil; Serge Mignani, Chatenay-Malabry, all of (FR)

(73) Assignee: Aventis Pharma S.A., Anthony Cedex (FR)

( * ) Notice: Subject to any disclaimer, the term of this patent is extended or adjusted under 35 U.S.C. 154(b) by 0 days.

(21) Appl. No.: 09/758,409

(22) Filed: Jan. 11, 2001

Related U.S. Application Data

(63) Continuation of application No. PCT/FR99/01719, filed on Jul. 13, 1999.

(30) Foreign Application Priority Data

Jul. 16, 1998 (FR) .............................. 98 09088

(51) Int. Cl.⁷ .................. A61K 31/4965; C07D 241/12
(52) U.S. Cl. ..................... 514/252.1; 544/336
(58) Field of Search ........................ 544/336; 514/252.1

(56) References Cited

FOREIGN PATENT DOCUMENTS

| JP | 53-90401 | * | 8/1978 |
| WO | 9728813 | | 8/1997 |

OTHER PUBLICATIONS

Shigematsu et al. Chemical Abstracts, vol. 90, No. 19276 (1978).*

* cited by examiner

*Primary Examiner*—Emily Bernhardt
(74) *Attorney, Agent, or Firm*—Balaram Gupta

(57) ABSTRACT

The invention concerns medicines containing as active principle at least a compound of formula (I):

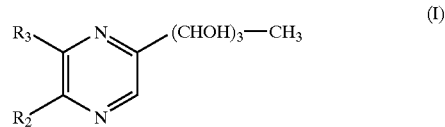

wherein either $R_2$ represents a $-CH_2-(CHOH)_2-CH_3$ chain and $R_3$ represents a hydrogen atom or $R_2$ represents a hydrogen atom and $R_3$ represents a $-CH_2-(CHOH)_2-CH_3$ chain or one of its stereoisomers or one of its salts, the novel compounds of formula (I), their stereoisomers, their salts and their preparation.

15 Claims, No Drawings

POLYHYDROXYALKYLPYRAZINE DERIVATIVES AND THEIR PREPARATION AND MEDICINES CONTAINING THEM

This application is a continuation of International application No. PCT/FR99/01719, filed Jul. 13, 1999; which claims the benefit of priority of French Patent Application No. 98/09,088, filed Jul. 16, 1998.

The present invention relates to medicaments comprising, as active principle, at least one compound of formula (I):

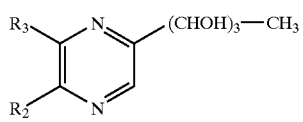

or one of its stereoisomers or one of its salts with an inorganic or organic acid, to novel compounds of formula (I), to their stereoisomers, to their salts with an inorganic or organic acid and to their preparation.

In the formula (I) either $R_2$ represents a —$CH_2$—(CHOH)$_2$—$CH_3$ chain and $R_3$ represents a hydrogen atom or $R_2$ represents a hydrogen atom and $R_3$ represents a —$CH_2$—(CHOH)$_2$—$CH_3$ chain.

The compounds of formula (I) comprising several asymmetric carbons exhibit stereoisomeric forms. These various stereoisomers form part of the invention.

The preferred medicaments according to the invention are those which comprise, as active ingredient, at least one compound of formula (I) chosen from:

1-[5-(2R,3S-dihydroxybutyl)pyrazin-2-yl]butane-1S,2S,3S-triol
1-[5-(2R,3R-dihydroxybutyl)pyrazin-2-yl]butane-1S,3S,3R-triol
1-[5-(2S,3S-dihydroxybutyl)pyrazin-2-yl]butane-1S,2R,3S-triol
1-[5-(2S,3R-dihydroxybutyl)pyrazin-2-yl]butane-1S,2R,3R-triol
1-[5-(2R,3S-dihydroxybutyl)pyrazin-2-yl]butane-1R,2S,3S-triol
1-[5-(2R,3R-dihydroxybutyl)pyrazin-2-yl]butane-1R,2S,3R-triol
1-[5-(2S,3S-dihydroxybutyl)pyrazin-2-yl]butane-1R,2R,3S-triol
1-[5-(2S,3R-dihydroxybutyl)pyrazin-2-yl]butane-1R,2R,3R-triol
1-[6-(2R,3S-dihydroxybutyl)pyrazin-2-yl]butane-1S,2S,3S-triol
1-[6-(2R,3R-dihydroxybutyl)pyrazin-2-yl]butane-1S,2S,3R-triol
1-[6-(2S,3S-dihydroxybutyl)pyrazin-2-yl]butane-1S,2R,3S-triol
1-[6-(2S,3R-dihydroxybutyl)pyrazin-2-yl]butane-1S,2R,3R-triol
1-[6-(2R,3S-dihydroxybutyl)pyrazin-2-yl]butane-1R,2S,3S-triol
1-[6-(2R,3R-dihydroxybutyl)pyrazin-2-yl]butane-1R,2S,3R-triol
1-[6-(2S,3S-dihydroxybutyl)pyrazin-2-yl]butane-1R,2R,3S-triol
1-[6-(2S,3R-dihydroxybutyl)pyrazin-2-yl]butane-1R,2R,3R-triol and their salts with an inorganic or organic acid.

The particularly preferred medicaments are those which comprise, as active principle, at least one compound of formula (I) chosen from the following:

1-[6-(2S,3S-dihydroxybutyl)pyrazin-2-yl]butane-1S,2R,3S-triol
1-[6-(2R,3R-dihydroxybutyl)pyrazin-2-yl]butane-1R,2S,3R-triol
1-[6-(2R,3S-dihydroxybutyl)pyrazin-2-yl]butane-1S,2S,3S-triol
1-[5-(2R,3S-dihydroxybutyl)pyrazin-2-yl]butane-1S,2S,3S-triol and their salts with an inorganic or organic acid.

It has been reported in the literature that the compounds of following formula (I) can be made by the reaction of rhamnose and ammonia or ammonium salt of organic acid (Patent JP78-90401):

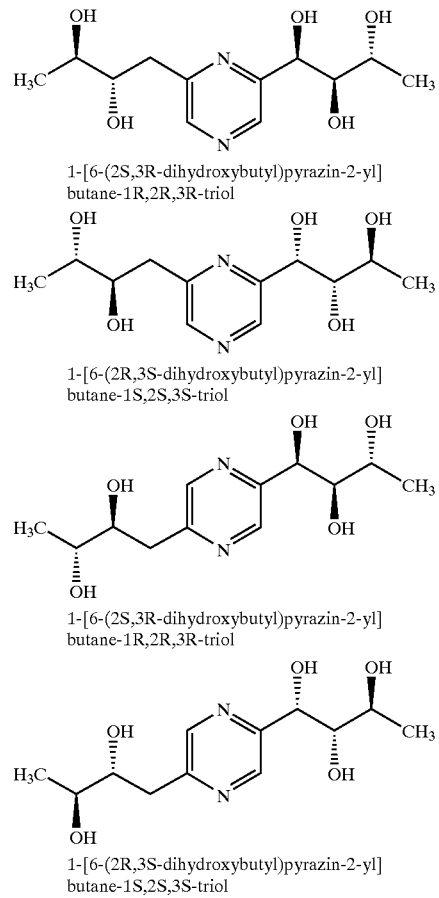

No pharmacological activity is described for any of these derivatives.

The other compounds of formula (I), their stereoisomers and their salts with an inorganic or organic acid are novel and also form part of the invention.

The preferred compounds of formula (I) are the following compounds:

1-[6-(2S,3S-dihydroxybutyl)pyrazin-2-yl]butane-1S,2R,3S-triol
1-[6-(2R,3R-dihydroxybutyl)pyrazin-2-yl]butane-1R,2S,3R-triol and their salts with an inorganic or organic acid.

The compounds of formula (I) can be prepared by reaction of ammonium formate with one or two aldoses of formula (II):

$$H_3C—(CHOH)_3—CHOH—CHO \quad (II)$$

or one of its stereoisomers.

This reaction is generally carried out in aqueous medium, at a temperature of between 20° C. and 100° C.

The aldoses $H_3C—(CHOH)_3—CHOH—CHO$ and their stereoisomers are commercially available or can be prepared from:

a) commercially available aldoses:
  by epimerization reactions, by application or adaptation of the methods described in Adv. Carbohydr. Chem., 13, 63, (1958), in particular in basic medium by means of a dilute aqueous sodium hydroxide solution (0.03 to 0.05%), at a temperature of between 20 and 40° C.,
  by chain-extension reactions, by application or adaptation of the methods described in "The Carbohydrates", edited by W. Pigman and D. Horton, Academic Press, New York, Volume IA, 133 (1972) and in particular by forming the cyanohydrin of the starting aldose (for example, by reaction with sodium cyanide in aqueous solution, at a temperature of between 10 and 30° C. and in the presence of sodium hydroxide, at a pH in the region of 9), then hydrolysis of the nitrile functional group thus formed to the corresponding acid by application or adaptation of the methods described in Organic Synthesis, Volume I, page 436 and Volume III, page 85 (for example, using concentrated sulphuric acid or hydrochloric acid, in aqueous solution, at a temperature of between 20° C. and the boiling temperature of the reaction mixture), and then reduction of the carboxylic acid functional group to the corresponding aldehyde by application or adaptation of the methods described in J. Am. Chem. Soc., 71, 122 (1949), in particular using an alkali metal borohydride (for example, sodium borohydride), in aqueous solution, at a temperature of between 20° C. and the boiling temperature of the reaction mixture, by chain-shortening reactions, by application or adaptation of the methods described in "The Carbohydrates", edited by W. Pigman and D. Horton, Academic Press, New York, Volume IB, 1980, page 929 or Chem. Ber., 83, 559 (1950) and in particular by converting the aldehyde functional group of the aldose to the corresponding hydroxylamine by application or adaptation of the methods described in Organic Synthesis, Volume II, page 314 (for example, using hydroxylamine hydrochloride, in aqueous solution and in the presence of a base, such as sodium carbonate, at a temperature of between 20 and 50° C.), and then reaction with 3,4-dinitrofluorobenzene in the presence of carbon dioxide and a base, such as sodium hydrogencarbonate, in aqueous solution, and an aliphatic alcohol (for example, isopropyl alcohol), at a temperature of between 50 and 80° C.,
  by deoxygenation reactions, by application or adaptation of the methods described in Carbohydr. Res., 36, 392 (1974) and 28D, 357 (1996), in particular by converting an alcohol functional group of the aldose to the corresponding sulfonate by application or adaptation of the methods described in Carbohydr. Res., 54, 105 (1977) and in J. Carbohydr. Chem., 6, 169 (1987) and 6, 537 (1987), for example using methanesulfonyl or p-toluenesulfonyl chloride in the presence of a base, and then the action of sodium borohydride or of lithium aluminium hydride in a solvent, such as respectively dimethyl sulfoxide, on the one hand, or benzene and diethyl ether, on the other hand, at a temperature of between 20° C. and the boiling temperature of the reaction mixture, b) corresponding allyl alcohols, by application or adaptation of the methods described in Science, 220, 949 (1983) and in particular using tert-butyl hydroperoxide in the presence of a titanium(IV) complex, such as the titanium(IV) isopropoxide and optically pure dialkyl tartrate (for example, diethyl tartrate) complex, followed by successive reaction with sodium thiophenolate, para-chloroperbenzoic acid in acetic anhydride, and diisopropylaluminum hydride.

The reaction mixtures obtained by the various processes described above are treated according to conventional physical (evaporation, extraction, distillation, chromatography or crystallisation, for example) or chemical (formation of salts, for example) methods.

The compounds of formula (I) can optionally be converted to addition salts with an inorganic or organic acid by the action of such an acid in an organic solvent, such as an alcohol, a ketone, an ether or a chlorinated solvent.

These salts also form part of the invention. Mention may be made, as examples of pharmaceutically acceptable salts, of the addition salts with inorganic or organic acids, such as acetate, propionate, succinate, benzoate, fumarate, maleate, oxalate, methanesulfonate, isethionate, theophyllineacetate, salicylate, methylenebis-(-hydroxynaphthoate), hydrochloride, sulphate, nitrate and phosphate.

The following examples illustrate the invention:

EXAMPLE 1

A solution of 10.0 g of L-fucose and 19.2 g of ammonium formate in 30 cc of water is heated at reflux for 6 hours and then allowed to cool to room temperature. The mixture is concentrated under reduced pressure (2.7 kPa) at a temperature of 50° C. The chestnut-brown pasty residue is taken up in 50 cc of ethanol, triturated and filtered and the insoluble fraction is washed with ethanol (operation repeated once). The filtrate is concentrated under reduced pressure (2.7 kPa) at a temperature of 50° C. to give a brown paste, which is purified by chromatography on a silica column (0.020–0.045 mm) at a pressure of approximately $1.5 \times 10^5$ Pa, elution being carried out with a chloroform/methanol/aqueous ammonia solution (12/6/1 by volume) mixture. The fractions comprising the expected product are combined and concentrated under reduced pressure (2.7 kPa) at a temperature of 50° C. The brown paste obtained is taken up in 3 cc of ethanol and is then reconcentrated under reduced pressure (2.7 kPa) at a temperature in the region of 50° C. to give the chestnut-brown paste. After lyophilization, 1.23 g of 1-[6-(2S,3S-dihydroxybutyl)-pyrazin-2-yl]butane-1S,2R,3S-triol are obtained in the form of a beige solid [$^1$H NMR spectrum (400 MHz, d6-$(CD_3)_2SO$, δ in ppm): 1.10 and 1.12 (2 d, J=6 Hz, each 3H, 2d $CH_3$ and 6d $CH_3$), 2.76 and 2.91 (2 dd, respectively J=14 and 9 Hz and J=14 and 3 Hz, each 1H, 6α $CH_2$), 3.49 (mt, 1H, 2β CH), 3.59 (mt, 1H, 6γ CH), 3.70 (mt, 1H, 6β CH), 3.86 (mt, 1H, 2γ CH), 4.31 (broad d, J=5 Hz, 1H, OH at 2γ), 4.42 (d, J=7 Hz, 1H, OH at 2β), 4.55 (mt, 2H, OH at 6b and OH at 6γ), 4.61 (dd, J=7 and 5 Hz, 1H, 2α CH), 5.49 (broad d, J=5 Hz, 1H, OH at 2α), 8.40 (s, 1H, =CH at 5), 8.48 (s, 1H, =CH at 3). $a_D^{20}$=−37.6° +/− 1.0 (c=0.5, methanol)].

EXAMPLE 2

A solution of 2 g of α-L-rhamnose and 7 g of ammonium formate in 8 cc of water is heated at reflux for 0.5 hour and then allowed to cool to room temperature. The mixture is filtered and then the filtrate is concentrated under reduced pressure (2.7 kPa) at a temperature of 45° C. The residue is three times taken up in diethyl ether and evaporated. The pasty solid thus obtained is extracted twice with 200 cc of acetone. The extracted solution is concentrated under reduced pressure (2.7 kPa) at a temperature of 45° C., the residue is taken up in 100 cc of ethanol and filtered, and the filtrates are combined. The combined filtrate is concentrated under reduced pressure (2.7 kPa) at a temperature of 45° C. and then the residue is taken up in dichloromethane. The precipitate is filtered off to give a brown solid. The latter is chromatographed on a silica column (0.040–0.063 mm) eluted with an ethyl acetate/methanol/acetic acid 6/1/1 by volume) mixture.

A—The fractions comprising the product with an rf. in the region of 0.3 are combined and concentrated under reduced pressure (2.7 kPa) at a temperature of 40° C. The oil thus obtained is again chromatographed on a silica column (0.040–0.063 mm) eluted with an ethyl acetate/ethanol/aqueous ammonia solution/water (40/10/2/2 by volume) mixture. The fractions comprising the expected product are combined and concentrated under reduced pressure (2.7 kPa) at a temperature of 40° C. The oil thus obtained is triturated in diethyl ether and then taken up in a small amount of ethanol, and the precipitate which is formed is filtered off. 64 mg of 1-[6-(2R,3S-dihydroxybutyl)pyrazin-2-yl]butane-1S,2S,3S-triol are thus isolated in the form of a white powder [$^1$H NMR spectrum (400 MHz, d6-(CD$_3$)2SO, δ in ppm): 1.13 (d, J=6.5 Hz, 3H, 6δ CH$_3$), 1.16 (d, J=6.5 Hz, 3H, 2δ CH$_3$), 2.66 and 3.04 (2 dd, respectively J=14 and 9 Hz and J=14 and 4 Hz, each 1H, 6α CH$_2$), from 3.30 to 3.40 (mt, 1H corresponding to the 2β CH), 3.48 (mt, 1H, 6γ CH), 3.58 (mt, 1H, 6β CH), 3.71 (mt, 1H, 2γ CH), 4.44 (d, J=8 Hz, 1H, OH at 2β), from 4.60 to 4.70 (mt, 3H, OH at 6β, OH at 6γ and OH at 2γ), 4.45 (broad d, J=6.5 Hz, 1H, 2α CH), 5.28 (d, J=6.5 Hz, 1H, OH at 2α), 8.34 (s, 1H, =CH at 5), 8.55 (s, 1H, =CH at 3).

B—The fractions comprising the product with an rf. in the region of 0.35 are combined and concentrated under reduced pressure (2.7 kPa) at a temperature in the region of 40° C. The oil thus obtained is again chromatographed on a silica column (0.040–0.063 mm) eluted with a 40/10/2/2 by volume ethyl acetate/ethanol/aqueous ammonia solution/water mixture. The fractions comprising the expected product are combined and concentrated under reduced pressure (2.7 kPa) at a temperature in the region of 40° C. The oil thus obtained is triturated in diethyl ether and then taken up in a small amount of ethanol, and the precipitate which is formed is filtered off. 48 mg of 1-[5-(2R,3S-dihydroxybutyl)pyrazin-2-yl]butane-1S,2S,3S-triol are thus isolated in the form of a white powder. $^1$H NMR spectrum (400 MHz, d6-(CD$_3$)$_2$SO, d in ppm): 1.12 (d, J=6 Hz, 3H, 5d CH$_3$), 1.15 (d, J=6 Hz, 3H, 2d CH$_3$), 2.69 and 3.05 (2 dd, respectively J=14 and 9 Hz and J=14 and 4 Hz, each 1H, 5a CH$_2$), from 3.30 to 3.45 (mt, 1H, 2b CH), 3.49 (mt, 1H, 5g CH), 3.61 (mt, 1H, 5b CH), 3.70 (mt, 1H, 2g CH), 4.47 (d, J=8 Hz, 1H, OH at 2b), from 4.55 to 4.80 (mt, 3H, OH at 2g, OH at 5b and OH at 5g), 4.45 (broad d, J=5.5 Hz, 1H, 2a CH), 5.27 (d, J=5.5 Hz, 1H, OH at 2a), 8.42 (s, 1H, =CH at 6), 8.65 (s, 1H, =CH at 3).

EXAMPLE 3

A solution of 3.28 g of D-fucose and 6.31 g of ammonium formate in 12 cc of water is heated at reflux for 2 hours and then allowed to cool to room temperature. The mixture is concentrated under reduced pressure (2.7 kPa) at a temperature of 55° C. The pasty residue is taken up in 70 cc of ethanol, triturated and filtered and the insoluble fraction is washed with ethanol (operation repeated three times). The filtrate is concentrated under reduced pressure (2.7 kPa) at a temperature in the region of 50° C. to give a brown oil (1.8 g) which is purified by chromatography on a silica column (0.020–0.045 mm), elution being carried out with a chloroform/methanol/aqueous ammonia solution (12/6/1 by volume) mixture and 50 cc fractions being collected. The fractions comprising the expected product are combined and concentrated under reduced pressure (2.7 kPa) at a temperature of 50° C. The brown paste obtained is chromatographed a second time under the same conditions. The fractions comprising the expected product are combined and concentrated under reduced pressure (2.7 kPa) at a temperature of 50° C. The oil obtained is taken up in 8 cc of distilled water and the solution is filtered. After lyophilization, 0.25 g of 1-[6-(2R,3R-dihydroxybutyl)pyrazin-2-yl]butane-1R,2S,3R-triol is obtained in the form of a beige solid [$^1$H NMR spectrum (400 MHz, d6-(CD$_3$)$_2$SO, at a temperature of 353 K, δ in ppm): 1.14 (d, J=7 Hz, 3H, 6δ CH$_3$), 1.16 (d, J=7 Hz, 3H, 2δ CH$_3$), 2.82 and 2.97 (2 dd, respectively J=14 and 9 Hz and J=14 and 4 Hz, each 1H, 6α CH$_2$), 3.56 (mt, 1H, 2βCH); 3.63 (mt, 1H, 6γ CH), 3.76 (mt, 1H, 6β CH), 3.88 (mt, 1H, 2γ CH), from 3.90 to 4.30 (unresolved peak, 4H, OH), 4.67 (d, J=7 Hz, 1H, 2α CH), 5.18 (unresolved peak, 1H, OH), 8.41 (s, 1H, =CH at 5), 8.52 (s, 1H, =CH at 3)].

The compounds of formula (I) exhibit advantageous pharmacological properties. They are of hypoglycemic type.

The hypoglycemic activity of the compounds of formula (I) was determined with respect to the hyperglycemic response to the oral administration of glucose in the normoglycemic mouse, according to the following protocol:

Swiss albinos mice weighing between 22 and 26 g are left without nourishment for 2 hours. At the end of this period, the glycemia is measured and, immediately after, a dose of glucose (2 g/kg) is administered orally. Thirty minutes later, the glycemia is once again measured. The mice which respond by a hyperglycemia greater than 170 mg/dl are selected and used to detect the hypoglycemic activity of the compounds according to the invention.

The mice thus chosen are divided into groups of at least 10 animals. Separate groups receive a solution of 3 to 50 mg/kg of the test product in a vehicle, such as water or a mixture of methylcellulose/tween and water, once daily by gastric intubation. The treatment lasts 4 days. On the 4th day, after the final treatment, the animals receive a dose of glucose (2 g/kg) and the glycemia is measured 20 to 40 minutes later. The percentage of inhibition of the hyperglycemic response to the administration of glucose is calculated with respect to the response measured in the group treated with the vehicle.

In this test, the compounds according to the invention exhibit a percentage of inhibition of glycemia of greater than or equal to 10%.

The compounds of general formula (I) according to the invention exhibit a low toxicity. Their LD$_{50}$ is greater than 2000 mg/kg via the oral route in the mouse.

In human therapeutics, these products are useful in the prevention and treatment of diabetes and in particular type II diabetes (NID diabetes), obese diabetes, diabetes at the age of about fifty, metaplethoric diabetes, diabetes affecting the elderly and mild diabetes. They can be used as a supplement to insulin therapy in insulin-dependent diabetes where they make it possible to gradually reduce the dose of insulin, unstable diabetes, insulin-resistant diabetes, and as a supplement to hypoglycemic sulphamides when these do not provide a sufficient decrease in glycemia. These products can also be used in complications of diabetes, such as hyperlipaemias, lipid metabolism disorders, dyslipaemias and obesity. They are also useful in the prevention and treatment of lesions of atherosclerosis and their complications (coronopathies, myocardial infarction, cardiomyopathies, progression of these three complications into left ventricular insufficiency, various arteriopathies, arterites of the lower limbs with claudication and progression into ulcers and gangrene, cerebral vascular insufficiency and its complications and sexual impotence of vascular origin), diabetic retinopathy and all its manifestations (increase in capillary permeability, capillary thrombosis and dilation, microaneurysms, arteriovenous shunt, venous dilation, punctiform and macular haemorrhages, exudates, macular oedemas, manifestations of proliferative retinopathy: neovessels, proliferative retinitis scars, haemorrhages of the vitreous body, retinal detachment), diabetic cataract, diabetic neuropathy in its various forms (peripheral polyneuropathies and their manifestations, such as paraesthesias, hyperaesthesias and pain, mononeuropathies, radiculopathies, autonomous neuropathies, diabetic amyotrophies), manifestations of diabetic foot (ulcers of the lower extremities and of the foot), diabetic nephropathy in its two diffuse and nodular forms, atheromatosis (rise in HDL lipoproteins promoting the elimination of cholesterol from the atheroma plaques, decrease in the LDL lipoproteins, decrease in the LDL/HDL ratio, inhibition of oxidation of the LDLs, decrease in plaque adhesiveness), hyperlipaemias and dyslipaemias (hypercholesterolaemias, hypertriglyceridaemias, normalization of the fatty acid level, normalization of uricaemia, normalization of the A and B apoproteins), cataracts, arterial hypertension and its consequences.

The medicaments according to the invention are composed of a compound according to the invention or a combination of these products, in the pure state or in the form of a composition in which it is combined with any other pharmaceutically compatible product, which can be inert or physiologically active. The medicaments according to the invention can be employed orally, parenterally, rectally or topically.

As solid compositions for oral administration, there can be used tablets, pills, powders (gelatin capsules, cachets) or granules. In these compositions, the active principle according to the invention is mixed with one or more inert diluents, such as starch, cellulose, sucrose, lactose or silica, under an argon stream. These compositions can also comprise substances other than the diluents, for example one or more lubricants such as magnesium stearate or talc, a colorant, a coating (dragees) or a glaze.

As liquid compositions for oral administration, there can be used pharmaceutically acceptable solutions, suspensions, emulsions, syrups and elixirs containing inert diluents, such as water, ethanol, glycerol, vegetable oils or liquid paraffin. These compositions can comprise substances other than the diluents, for example wetting, sweetening, thickening, flavouring or stabilising products.

The sterile compositions for parenteral administration can preferably be solutions in aqueous or nonaqueous form, suspensions or emulsions. As solvent or vehicle, there can be employed water, propylene glycol, a polyethylene glycol, vegetable oils, in particular olive oil, injectable organic esters, for example ethyl oleate, or other suitable organic solvents. These compositions can also contain adjuvants, in particular wetting, isotonizing emulsifying, dispersing and stabilising agents. Sterilisation can be performed in several ways, for example by aseptizing filtration, by incorporating sterilising agents into the composition, by irradiation or by heating. They can also be prepared in the form of sterile solid compositions which can be dissolved at the time of use in sterile water or any other injectable sterile medium.

The compositions for rectal administration are suppositories or rectal capsules which contain, in addition to the active product, excipients such as cocoa butter, semisynthetic glycerides or polyethylene glycols.

The compositions for topical administration can be, for example, creams, lotions, collyria, collutoria, nose drops or aerosols.

The doses depend on the desired effect, the duration of treatment and the administration route used; they are generally between 150 mg and 600 mg per day via the oral route for an adult with unit doses ranging from 50 mg to 200 mg of active substance.

In general, the doctor will determine the appropriate dosage according to the age, weight and all other factors specific to the subject to be treated.

The following examples illustrate compositions according to the invention:

EXAMPLE A

Hard gelatin capsules, with doses of 50 mg of active product, having the following composition are prepared according to the usual technique:

Active product 50 mg

Cellulose 18 mg

Lactose 55 mg

Colloidal silica 1 mg

Sodium carboxymethylstarch 10 mg

Talc 10 mg

Magnesium stearate 1 mg

EXAMPLE B

Tablets, with doses of 50 mg of active product, having the following composition are prepared according to the usual technique:

Active product 50 mg

Lactose 104 mg

Cellulose 40 mg

Polyvidone 10 mg

Sodium carboxymethylstarch 22 mg

Talc 10 mg

Magnesium stearate 2 mg

Colloidal silica 2 mg

Hydroxymethylcellulose, glycerol, titanium oxide (72/3.5/24.5) mixture qs for 1 finished film-coated tablet containing 245 mg

EXAMPLE C

An injectable solution containing 50 mg of active product having the following composition is prepared:

Active product 50 mg

Benzoic acid 80 mg

Benzyl alcohol 0.06 ml

Sodium benzoate 80 mg

Ethanol at 95% 0.4 ml
Sodium hydroxide 24 mg
Propylene glycol 1.6 ml
Water for 4 ml The invention also relates to the use of the compounds of general formula (I), their stereoisomers and their salts with an inorganic or organic acid in the preparation of pharmaceutical compositions of use in the treatment or prevention of diabetes and complications of diabetes.

What is claimed is:

1. A pharmaceutical composition comprising, as active principle, at least one compound of formula (I):

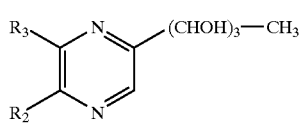

wherein
either $R_2$ represents a —$CH_2$—$(CHOH)_2$—$CH_3$ chain and $R_3$ represents a hydrogen atom or $R_2$ represents a hydrogen atom and $R_3$ represents a —$CH_2$—$(CHOH)_2$—$CH_3$ chain, or one of its sterioisomers or one of its salts with a pharmaceutically acceptable inorganic or organic acid, in combination with at least one pharmaceutically acceptable carrier.

2. The composition according to claim 1 comprising, as active principle, at least one compound chosen from the following:

1-[5-(2R,3S-dihydroxybutyl)pyrazin-2-yl]butane-1S,2S,3S-triol
1-[5-(2R,3R-dihydroxybutyl)pyrazin-2-yl]butane-1S,2S,3R-triol
1-[5-(2S,3S-dihydroxybutyl)pyrazin-2-yl]butane-1S,2R,3S-triol
1-[5-(2S,3R-dihydroxybutyl)pyrazin-2-yl]butane-1S,2R,3R-triol
1-[5-(2R,3S-dihydroxybutyl)pyrazin-2-yl]butane-1R,2S,3S-triol
1-[5-(2R,3R-dihydroxybutyl)pyrazin-2-yl]butane-1R,2S,3R-triol
1-[5-(2S,3S-dihydroxybutyl)pyrazin-2-yl]butane-1R,2R,3S-triol
1-[5-(2S,3R-dihydroxybutyl)pyrazin-2-yl]butane-1R,2R,3R-triol
1-[6-(2R,3S-dihydroxybutyl)pyrazin-2-yl]butane-1S,2S,3S-triol
1-[6-(2R,3R-dihydroxybutyl)pyrazin-2-yl]butane-1S,2S,3R-triol
1-[6-(2S,3S-dihydroxybutyl)pyrazin-2-yl]butane-1S,2R,3S-triol
1-[6-(2S,3R-dihydroxybutyl)pyrazin-2-yl]butane-1S,2R,3R-triol
1-[6-(2R,3S-dihydroxybutyl)pyrazin-2-yl]butane-1R,2S,3S-triol
1-[6-(2R,3R-dihydroxybutyl)pyrazin-2-yl]butane-1R,2S,3R-triol
1-[6-(2S,3S-dihydroxybutyl)pyrazin-2-yl]butane-1R,2R,3S-triol
1-[6-(2S,3R-dihydroxybutyl)pyrazin-2-yl]butane-1R,2R,3R-triol or one of their stereoisomers or one of their salts with a pharmaceutically acceptable inorganic or organic acid.

3. The composition according to claim 1 comprising, as active principle, at least one compound chosen from the following:

1-[6-(2S,3S-dihydroxybutyl)pyrazin-2-yl]butane-1S,2R,3S-triol
1-[6-(2R,3R-dihydroxybutyl)pyrazin-2-yl]butane-1R,2S,3R-triol
1-[6-(2R,3S-dihydroxybutyl)pyrazin-2-yl]butane-1S,2S,3S-triol
1-[5-(2R,3S-dihydroxybutyl)pyrazin-2-yl]butane-1S,2S,3S-triol or one of their salts with a pharmaceutically acceptable inorganic or organic acid.

4. A compound of formula:

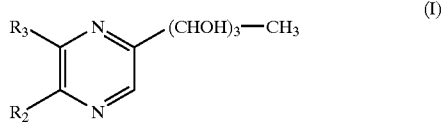

wherein either $R_2$ represents a —$CH_2$—$(CHOH)_2$—$CH_3$ chain and $R_3$ represents a hydrogen atom or $R_2$ represents a hydrogen atom and $R_3$ represents a —$CH_2$—$(CHOH)_2$—$CH_3$ chain, or one of its stereoisomers or one of its pharmaceutically acceptable salts with an inorganic or organic acid, with the exception of the following products:

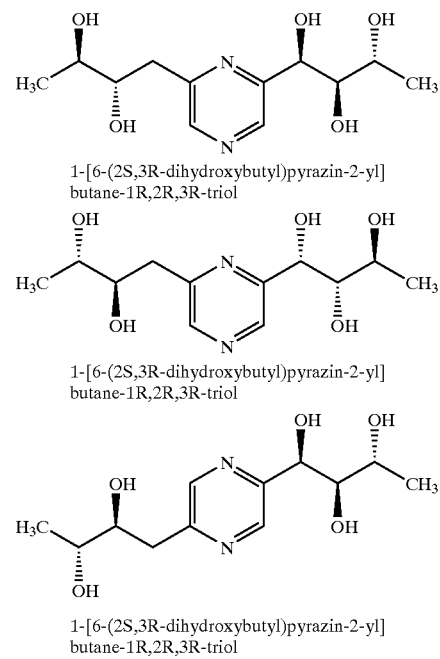

1-[6-(2S,3R-dihydroxybutyl)pyrazin-2-yl]
butane-1R,2R,3R-triol

1-[6-(2S,3R-dihydroxybutyl)pyrazin-2-yl]
butane-1R,2R,3R-triol

1-[6-(2S,3R-dihydroxybutyl)pyrazin-2-yl]
butane-1R,2R,3R-triol

-continued

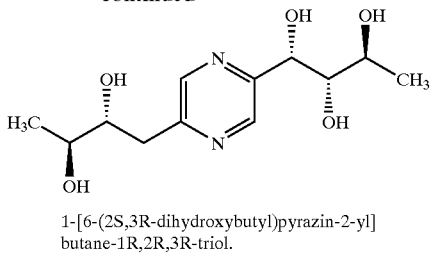

1-[6-(2S,3R-dihydroxybutyl)pyrazin-2-yl]
butane-1R,2R,3R-triol.

5. The Compound of formula (I) according to claim 4, selected from the group consisting of:

1-[5-(2R,3R-dihydroxybutyl)pyrazin-2-yl]butane-1S,2S,3R-triol
1-[5-(2S,3S-dihydroxybutyl)pyrazin-2-yl]butane-1S,2R,3S-triol
1-[5-(2S,3R-dihydroxybutyl)pyrazin-2-yl]butane-1S,2R,3R-triol
1-[5-(2R,3S-dihydroxybutyl)pyrazin-2-yl]butane-1R,2S,3S-triol
1-[5-(2R,3R-dihydroxybutyl)pyrazin-2-yl]butane-1R,2S,3R-triol
1-[5-(2S,3S-dihydroxybutyl)pyrazin-2-yl]butane-1R,2R,3S-triol
1-[6-(2R,3R-dihydroxybutyl)pyrazin-2-yl]butane-1S,2S,3R-triol
1-[6-(2S,3S-dihydroxybutyl)pyrazin-2-yl]butane-1S,2R,3S-triol
1-[6-(2S,3R-dihydroxybutyl)pyrazin-2-yl]butane-1S,2R,3R-triol
1-[6-(2R,3S-dihydroxybutyl)pyrazin-2-yl]butane-1R,2S,3S-triol
1-[6-(2R,3R-dihydroxybutyl)pyrazin-2-yl]butane-1R,2S,3R-triol and
1-[6-(2S,3S-dihydroxybutyl)pyrazin-2-yl]butane-1R,2R,3S-triol or a pharmaceutically acceptable inorganic or organic acid addition salt thereof.

6. A Compound selected from the group consisting of:

1-[6-(2S,3S-dihydroxybutyl)pyrazin-2-yl]butane-1S,2R,3S-triol
1-[6-(2R,3R-dihydroxybutyl)pyrazin-2-yl]butane-1R,2S,3R-triol
1-[6-(2R,3S-dihydroxybutyl)pyrazin-2-yl]butane-1R,2S,3S-triol and
1-[5-(2R,3S-dihydroxybutyl)pyrazin-2-yl]butane-1R,2S,3S-triol or a pharmaceutically acceptable inorganic or organic acid addition salt thereof.

7. The compound according to claim 6 which is 1-[6-(2S,3S-dihydroxybutyl)pyrazin-2-yl]butane-1S,2R,3S-triol or a pharmaceutically acceptable inorganic or organic acid addition salt thereof.

8. The compound according to claim 6 which is 1-[6-(2R,3R-dihydroxybutyl)pyrazin-2-yl]butane-1R,2S,3R-triol or a pharmaceutically acceptable inorganic or organic acid addition salt thereof.

9. The compound according to claim 6 which is 1-[6-(2R,3S-dihydroxybutyl)pyrazin-2-yl]butane-1R,2S,3S-triol or a pharmaceutically acceptable inorganic acid addition salt thereof.

10. The compound according to claim 6 which is 1-[5-(2R,3S-dihydroxybutyl)pyrazin-2-yl]butane-1R,2S,3S-triol or a pharmaceutically acceptable inorganic acid addition salt thereof.

11. A process for the preparation of the compounds of formula (I) according to claim 4, comprising the steps of:

a) reacting ammonium formate with one or two aldoses of formula (II):

$H_3C-(CHOH)_3-CHOH-CHO$     (II)

b) isolating the product and optionally
c) converting the product to a pharmaceutically acceptable salt by reacting with an inorganic or organic acid.

12. A method of treating or preventing diabetes in humans through the hypoglycemic activity of a drug comprising administering to a patient in need thereof a pharmaceutically effective amount of a compound of formula (I):

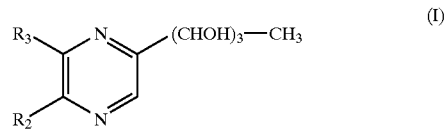

wherein either $R_2$ represents a $-CH_2-(CHOH)_2-CH_3$ chain and $R_3$ represents a hydrogen atom or $R_2$ represents a hydrogen atom and $R_3$ represents a $-CH_2-(CHOH)_2-CH_3$ chain, or one of its stereoisomers or one of its salts with a pharmaceutically acceptable inorganic or organic acid.

13. A method of treating diabetes in humans through the hypoglycemic activity of a drug comprising administering to a patient in need thereof a pharmaceutically effective amount of a compound of formula (I) according to claim 12.

14. A method of preventing diabetes in humans through the hypoglycemic activity of a drug comprising administering to a patient in need thereof a pharmaceutically effective amount of a compound of formula (I) according to claim 12.

15. A method of treating or preventing diabetes in humans through the hypoglycemic activity of a drug comprising administering to a patient in need thereof a pharmaceutically effective amount of one or more compounds selected from the group consisting of:

1-[6-(2S,3S-dihydroxybutyl)pyrazin-2-yl]butane-1S,2R,3S-triol
1-[6-(2R,3R-dihydroxybutyl)pyrazin-2-yl]butane-1R,2S,3R-triol
1-[6-(2R,3S-dihydroxybutyl)pyrazin-2-yl]butane-1S,2S,3S-triol and
1-[5-(2R,3S-dihydroxybutyl)pyrazin-2-yl]butane-1S,2S,3S-triol or one of their salts with a pharmaceutically acceptable inorganic or organic acid.

* * * * *